United States Patent [19]

Benkeser et al.

[11] Patent Number: 4,533,760

[45] Date of Patent: Aug. 6, 1985

[54] PROCESS FOR REDUCING ORGANIC COMPOUNDS WITH CALCIUM, AMINE, AND ALCOHOL

[75] Inventors: Robert A. Benkeser, West Lafayette, Ind.; James A. Laugal, Lostant, Ill.; Angela Rappa, Baltimore, Md.

[73] Assignee: Purdue Research Foundation, West Lafayette, Ind.

[21] Appl. No.: 643,649

[22] Filed: Aug. 23, 1984

[51] Int. Cl.$^3$ ............................................. C07C 5/10
[52] U.S. Cl. .................................. 568/667; 568/631; 585/266; 585/267; 585/271
[58] Field of Search ............... 585/266, 267, 268, 271, 585/272; 568/667, 631

[56] References Cited

U.S. PATENT DOCUMENTS 3,278,618  10/1966  Amagasa et al. .................. 585/267

FOREIGN PATENT DOCUMENTS 3731927   4/1965  Japan ................................. 585/267
40-48724  8/1965  Japan ................................. 585/267
1025426   4/1966  United Kingdom ................ 585/267

OTHER PUBLICATIONS

Benkeser et al., J. Org. Chem., 44, 3737–39, (1979).
Benkeser et al., J. Org. Chem., 48, 2796–2802, (1983).
Benkeser et al., Synth. Commun., 13, 1103–16, (1983).
Benkeser et al., Tetrahedron Lett., 25, 2089–92, (1984).

*Primary Examiner*—D. E. Gantz
*Assistant Examiner*—A. Pal
*Attorney, Agent, or Firm*—Barnes & Thornburg

[57] ABSTRACT

Olefins are produced by contacting an organic compound having at least one benzene ring with calcium metal, ethylenediamine, a low molecular weight aliphatic alcohol, and optionally a low molecular weight aliphatic primary amine, and/or an inert, abrasive particulate substance. The reduction is conducted at temperatures ranging from about −10° C. to about 30° C. or somewhat higher. Substantially all of the organic compounds are converted to corresponding cyclic olefins, primarily diolefins.

17 Claims, No Drawings

PROCESS FOR REDUCING ORGANIC COMPOUNDS WITH CALCIUM, AMINE, AND ALCOHOL

The Government has rights in this invention pursuant to Contract No. DE-AC02-81ER10989 awarded by the Department of Energy.

BACKGROUND OF THE INVENTION

1. Field of the Invention

This invention relates to the manufacture of cyclic polyolefinic hydrocarbons. It particularly relates to the reduction of organic compounds having at least one benzene ring in a calcium-amine-alcohol system to polyolefins of similar cyclic structures.

2. Description of the Prior Art

The principal method for reducing aromatic hydrocarbons is the Birch reduction method which employs sodium or lithium metal and liquid ammonia in the presence of an alcohol to produce diolefinic hydrocarbons. This process has the following disadvantages. Sodium metal is very reactive and requires a great deal of caution in use and handling. Liquid ammonia boils at $-33°$ C. and therefore is difficult to use on a large scale. It is obviously desirable to provide a safer and easier reduction process.

The reduction of aromaic compounds with calcium, ammonia, and ether has been reported by Dumanskii at al. *J. Russ. Phys. Chem. Soc.*, 48, 994, (1916)., Kazanskii et al. *J. Gen. Chem.* (USSR), 8, 642, (1938), and Campbell et al. *J. Am. Chem. Soc.*, 67, 282, (1945). The procedures reported by these workers are cumbersome and usually give products that are quite impure and difficult to separate. As a result, calcium reductions have never gained widespread acceptance and have been used only sporadically through the years.

The reduction of aromatic hydrocarbons by treatment with calcium metal in admixture with methylamine and ethylenediamine at $-2.5°$ C. is described by Benkeser et al. *J. Org. Chem.*, 44, 3737 (Oct. 12, 1979). Unlike the invention described herein, alcohol was not utilized in that reducing system. Likewise, the use of inert abrasive particles to remove insoluble coatings that mask the calcium surface was not taught by the process described in that publication.

Filed of even date herewith is a patent application, Ser. No. 643,442, by the same inventors directed to the reduction of the same class of starting materials in the presence of ethylenediamine (or other analogous alkylene polyamine) and a 100% stoichiometric excess or more of calcium metal at ambient or somewhat elevated temperatures. Alcohol is not used in the reducing system of the companion application, and a large excess of calcium is used therein to compensate for insoluble coatings that form on the calcium metal surface. As will be seen below, other methods and operating conditions are employed in the invention of the present application.

BRIEF SUMMARY OF THE INVENTION

It has now been discovered that organic compounds having at least one benzene ring can be reduced to structurally corresponding olefins in high yield by contacting such organic compounds with calcium metal, ethylenediamine, a low molecular weight aliphatic alcohol, and optionally a low molecular weight aliphatic primary amine, said contact being effected at a temperature from about $-10°$ C. to about 30° C. or somewhat higher, preverably 0° C.

The reduction process is made more effective by optionally including in the reaction mixture a quantity of inert abrasive particulate material whereby insoluble coatings that tend to form on the surface of the calcium metal are removed by the abrasive action of the inert particles. Moreover, the optional aliphatic primary amine in the reaction mixture tends to dissolve calcium amides or to inhibit their formation. Thus, the calcium metal is not deactivated by masking as in the prior art methods but fresh active calcium is continuously presented to the reaction mixture. As a result, the quantity of calcium required is minimized. Suitable abrasive materials include sand, silicon carbide, silica-alumina, diatomaceous earth, and the like. As will be seen, the calcium-amine-alcohol system is much more effective for the formation of polyolefins than prior art reduction systems.

The process of this invention, more fully described below, is effective in many cases to convert substantially all of the organic compounds having at least one benzene ring to corresponding cyclic polyolefins. It is to be noted that by the process of this invention organic compounds having at least one benzene ring are reduced by contacting such organic compounds with calcium metal, an amine mixture, and an alcohol. Thus, the reducing system of this invention clearly differs from that of the prior art lithium-ammonia, sodium-ammonia, lithium-amine, and calcium-amine systems.

DETAILED DESCRIPTION OF THE INVENTION

A wide variety of organic compounds, several of which are derived from coal, can be used as the starting material in this invention. Naphthalene, 1-methylnaphthalene, 2-methylnaphthalene, 1-methoxynaphthalene, 2-methoxynaphthalene, benzene, ethylbenzene, isopropylbenzene, t-butylbenzene, indan, cumene, xylene, tetralin, anthracene, anisole, diphenylmethane, 1,2-diphenylethane, and other substituted benzenes and naphthalenes and the like are suitable starting materials. Other organic compounds of the defined class can be effectively reduced as described herein; thus, the invention should not be construed as being applicable to only the designated compounds.

The calcium metal useful in this invention is preferably in the form of calcium turnings or calcium shot and preferably in the form of substantially pure calcium. Generally an excess of around 10% to around 25% calcium is sufficient to effect the desired reduction, based on the stoichiometric amounts necessary to effect complete reduction of the starting material, larger amounts being surplusage. In a preferred embodiment of the invention, calcium can be conserved by using inert abrasive particulates in combination with a high-shear stirrer to effectively remove such coatings from the calcium surfaces.

Suitable low molecular weight (i.e., $C_1$–$C_5$) aliphatic alcohols for use in this invention include methanol, ethanol, n-propyl alcohol, isopropyl alcohol, n-butyl alcohol, isobutyl alcohol, tert-butyl alcohol, n-amyl alcohol, isoamyl alcohol, tert-amyl alcohol, neopentyl alcohol, and the like. Other alcohols not specifically mentioned may be equally suitable or more suitable than these mentioned. The alcohol is suitably used in a molar ratio to the starting material between about 1:1 and about 3:1.

The amine solvent mixture used in the present invention comprises essentially ethylenediamine or a similar alkylene polyamine in combination with a low molecular weight aliphatic primary amine, for example, the $C_1$-$C_5$ aliphatic primary amines. Preferred low molecular weight aliphatic primary amines include n-butylamine, isobutylamine, tertiary butylamine, isopropylamine, neopentylamine, methylamine, and the like. The addition of the aliphatic primary amine to the mixture prevents the ethylenediamine from freezing out of solution at temperatures below 9° C. Another important characteristic of the amine solvent mixture is that the ratio of ethylenediamine and aliphatic primary amine can be varied to maximize the solubility of the starting material. The amine solvent mixture may also be supplemented with tetrahydrofuran (THF), diethyl ether, petroleum ether, or the like for the purpose of maximizing solubility of the organic compound starting material in the amine solvent mixture.

The reaction vessel is equipped with means for agitating the vessel contents and means for condensing amine solvents in order to prevent their evaporation from the reaction vessel. Prior to the addition of any chemical components, the reaction vessel is dried and may be purged, if desired, with an inert gas, such as nitrogen.

In a preferred form of the invention, the starting compound, calcium metal, and inert abrasive particles are commingled in a reaction vessel with approximately 25% of the intended quantity of alcohol, followed by freshly distilled aliphatic primary amine and dry ethylenediamine. The remaining quantity of alcohol is added at a subsequent stage, hereinafter described.

The reduction step is carried out at a temperature ranging from about −10° C. to about 30° C. or somewhat higher and preferably at a temperature of about 0° C., because the reduction process is much more selective at 0° C. than at higher temperatures.

The contents of the reaction vessel are agitated for a period of time sufficient to promote an even distribution of material within the reaction vessel and to initiate the reduction process. A period of time sufficient to effect such distribution may range from about 5 minutes to about 60 minutes. Following such initial period, the remaining quantity of alcohol is added to the reaction vessel in a controlled manner to allow the reaction temperature to be maintained at the desired level. The mixture is thereafter agitated for a period of time sufficient to reduce substantially all of the benzene ring or rings to a corresponding cyclic olefin. Such a time period will generally range from about 1 hour to about 30 hours, more usually from about 12 to about 24 hours. The reaction time will vary to some extent, depending on the organic starting material.

The reaction product mixture comprising reacted and unreacted starting material as well as unreacted calcium and calcium amides is conveniently worked up by dissolving the calcium and calcium amides in aqueous ammonium chloride. The olefinic product forms an organic phase, which is separated and fractionally distilled.

The reduction technique of this invention is quite competitive in both yield and purity with the various prior art reduction processes. Significant advantages of this invention, however, are that the starting materials are both safe and easy to handle as well as readily available. The use of the inert abrasive particles results in a reduced calcium consumption.

The following examples illustrate the application of the present invention to a variety of organic starting materials. These examples are given only for the purpose of illustration, and are not to be construed as limiting in any way.

EXAMPLE 1

Anthracene was reduced to 1,4,5,8,9,10-hexahydroanthracene by the following procedure in a mixture of calcium, t-butyl alcohol, n-butylamine, ethylenediamine and tetrahydrofuran.

A dry flask was equipped with a stirrer, a gas inlet tube, and an air-cooled condenser. The system was initially purged with argon, whereupon the following materials were added; calcium shot (0.1 g-atom), white sand (24 g), anthracene (0.025 mol), and t-butyl alcohol (0.05 mol). Ethylenediamine was dried by stirring over fresh sodium hydroxide pellets for 24 hours, refluxing for three hours over calcium oxide, and distilling. Freshly distilled ethylenediamine (38 ml), n-butylamine (38 ml), and tetrahydrofuran (THF) (90 ml) were added next and the flask was cooled to about 0° C. The mixture was stirred for 25 minutes, following which an additional quantity of t-butyl alcohol (0.15 mol) was slowly added. The mixture was then stirred for 24 hours at 0° C.

The following work-up procedure was utilized to recover the olefin products. Technical diethyl ether (100 ml) was added to the reaction product mixture, followed by careful addition of aqueous $NH_4Cl$ (27 g in 100 ml of $H_2O$). An ice bath was used to control the temperature during the hydrolysis step, which tended to be a vigorous reaction. After the reaction was complete the layers were separated and the aqueous layer extracted with two portions of diethyl ether. The organic extracts were combined with the organic phase from the reaction mixture, washed with two portions of water, two portions of 5% HCl, one portion of 5% $NaHCO_3$, and one portion of brine, and then dried over anhydrous $Na_2SO_4$. The solvent was removed by rotary evaporation.

The product was a yellow solid containing a mixture of 1,4,5,8,9,10-hexahydroanthracene (76%), 1,2,3,4,5,6,7,8,9,10-decahydroanthracene (6) and anthracene (2%). Recrystallization of the mixture from petroleum ether (30°–60° C.) yielded 63% of 1,4,5,8,9,10-hexahydroanthracene as a white solid melting at 146°–147° C.

EXAMPLE 2 p-Xylene was reduced to 1,4-dimethyl-1,4-cyclohexadiene of 92% purity, generally according to the procedure of Example 1. Calcium (0.3 g-atom), white sand (24 g), p-xylene (0.2 mol) and t-butyl alcohol (0.066 mol) were placed in a reaction flask which had been previously dried and flushed with argon. n-Butylamine (150 ml) and dry ethylenediamine (150 ml) were added, the flask was cooled to about 0° C., and the mixture was allowed to stir for 40 minutes. Additional t-butyl alcohol (0.534 mol) was added over a 40 minute period, and stirring was continued for 24 hours at 0° C. After the general workup described in Example 1, distillation yielded 63% of product boiling at 140°–142° C. Analysis by GLPC indicated the product to be 1,4-dimethyl-1,4-cyclohexadiene.

EXAMPLES 3-19

Additional organic compounds were reduced by a calcium-amine-t-butyl alcohol procedure generally similar to that of Examples 1 2. The results of these tests are given in Table 1. Organic starting materials were added to the reaction vessel in quantities of 25 mmol as in Example 1. Ethylenediamine and n-butylamine or methylamine were added in quantities of 38 ml each, as in Example 1. Calcium and alcohol were added in the quantities given in Table 1. The overall conversion for each of the starting materials was quite high, ranging from 90–95% of theory.

TABLE I

Reduction of Aromatic Compounds by Calcium, Ethylenediamine, n-Butylamine, and t-Butyl Alcohol Procedure

| Example No. | Organic Starting Material | Solvent | Calcium (g-atom) | Alcohol (mol) | Product |
|---|---|---|---|---|---|
| 1 | Anthracene | n-butylamine ethylenediamine | 0.1 | 0.6 | 1,4,5,8,9,10-hexahydroanthracene |
| 2 | p-Xylene | n-butylamine ethylenediamine | 0.3 | 0.2 | 1,4-dimethyl-1,4 cyclohexadiene |
| 3 | Naphthalene | n-butylamine ethylenediamine | 0.075 | 0.15 | 1,4,5,8-tetrahydronaphthalene, 1,2,3,4,5,8-hexahydronaphthalene |
| 4 | Tetralin | n-butylamine ethylenediamine | 0.05 | 0.1 | 1,2,3,4,5,8-hexahydronaphthalene |
| 5 | Anisole | n-butylamine ethylenediamine | 0.05 | 0.1 | 1-methoxy-1,4-cyclohexadiene |
| 6 | o-Xylene | n-butylamine ethylenediamine | 0.05 | 0.1 | 1,2-dimethyl-1,4-cyclohexadiene |
| 7 | m-Xylene | n-butylamine ethylenediamine | 0.05 | 0.1 | 1,5-dimethyl-1,4-cyclohexadiene |
| 8 | 1,3-dimethoxybenzene | n-butylamine ethylenediamine | 0.053 | 0.025 | 1,5-dimethoxy-1,4-cyclohexadiene 1-methoxy-1,4-cyclohexadiene |
| 9 | 1-methylnaphthalene | n-butylamine ethylenediamine | 0.05 | 0.1 | 1-methyl-5,6,7,8-tetrahydronaphthalene 1-methyl-5,8-dihydronaphthalene |
| 10 | 2-methylnaphthalene | n-butylamine ethylenediamine | 0.075 | 0.1 | 2-methyl-1,4,5,8-tetrahydronaphthalene 2-methyl-5,6,7,8-tetrahydronaphthalene |
| 11 | 1-methoxynaphthalene | n-butylamine ethylenediamine | 0.1 | 0.2 | 1-methoxy-5,8-dihydronaphthalene 1-methoxy-5,6,7,8-tetrahydronaphthalene |
| 12 | 2-methoxynaphthalene | n-butylamine ethylenediamine | 0.1 | 0.2 | 2-methoxy-1,4,5,8-tetrahydronaphthalene 1,4,5,8-tetrahydronaphthalene |
| 13 | diphenylmethane | n-butylamine ethylenediamine | 0.075 | 0.15 | bis(1,4-cyclohexadienyl) methane |
| 14 | diphenylethane | n-butylamine ethylenediamine | 0.075 | 0.15 | 1,2-bis(1,4-cyclohexadienyl) ethane |
| 15 | methylbenzene | methylamine ethylenediamine | 0.05 | 0.1 | 1-methyl-1,4-cyclohexadiene |
| 16 | ethylbenzene | methylamine ethylenediamine | 0.05 | 0.1 | 1-ethyl-1,4-cyclohexadiene |
| 17 | isopropylbenzene | methylamine ethylenediamine | 0.05 | 0.1 | 1-isopropyl-1,4-cyclohexadiene |
| 18 | t-butyl benzene | methylamine ethylenediamine | 0.05 | 0.1 | 1-t-butyl-1,4-cyclohexadiene |
| 19 | indan | n-butylamine ethylenediamine | 0.05 | 0.1 | 4,7-dihydroindan |

In a separate but related embodiment of the process of the present invention, one or more soluble salts are added to the reaction mixture, partly or wholly replacing the aliphatic primary amine for the purpose of maintaining the alkylene polyamine in solution at low temperatures. For this purpose, the sodium and calcium halides are especially suitable, such as sodium bromide or calcium chloride, and are satisfactorily used in a weight ratio to the alkylene polyamine between about 0.5:1 and about 1.5:1. Other salts include sodium chloride, sodium iodide, calcium fluoride, calcium bromide, and the like. Salts of other metals of the alkali-metal and alkaline-earth-metal groups may also be used, but are less attractive for economic reasons.

While we have described the invention with respect to specific starting materials, process steps, and operating conditions, it will be understood that such matters are illustrative only and are not intended by way of limitation. Numerous modifications and equivalents will be apparent to those of ordinary skill in the art without departing from the spirit of the invention.

What is claimed is:

1. A method for reducing an organic compound having at least one benzene ring and obtaining therefrom a cyclic olefin having the same structure as such organic compound except for degree of unsaturation, which comprises contacting such organic compound with a reaction mixture comprising calcium metal, ethylenediamine, and a low molecular weight aliphatic alcohol at a temperature of about $-10°$ C. to about 30° C., for a period of time sufficient to effect the said reduction, the proportion of calcium metal to such organic compound being at least about 10% in excess of the stoichiometric quantity necessary for complete reduction of such benzene ring, whereby a cyclic polyolefin is obtained having at least two double bonds.

2. The method of claim 1 wherein such contacting is effected by stirring in the presence of inert abrasive particulate matter whereby insoluble coatings that are formed on the surface of the calcium metal are effectively removed.

3. The method of claim 1 wherein the proportion of the said calcium metal is about 10% to about 25% in excess of the stoichiometric quantity necessary for complete reduction of such benzene ring.

4. The method of claim 1 wherein such organic compound is anthracene.

5. The method of claim 1 wherein such organic compound is anisole.

6. The method of claim 1 wherein such organic compound is p-xylene.

7. The method of claim 1 wherein such low molecular weight aliphatic alcohol is a $C_1$–$C_5$ aliphatic alcohol.

8. The method of claim 1 wherein such low molecular weight aliphatic alcohol is t-butyl alcohol.

9. The method of claim 1 wherein a low molecular weight aliphatic primary amine is included in the reaction mixture.

10. The method of claim 9 wherein the low molecular weight aliphatic primary amine is a $C_1$–$C_5$ aliphatic primary amine.

11. The method of claim 9 wherein the low molecular weight aliphatic primary amine is n-butylamine.

12. The method of claim 2 wherein such inert abrasive particulate matter is sand.

13. The method of claim 2 wherein such inert abrasive particulate matter is silicon carbide.

14. The method of claim 2 wherein such inert abrasive particulate matter is silica alumina.

15. The method of claim 2 wherein such organic compound is contacted with calcium metal, ethylenediamine, t-butyl alcohol, n-butylamine, and sand.

16. The method of claim 2 wherein such organic compound is contacted with calcium metal, ethylenediamine, t-butyl alcohol, methylamine, and sand.

17. The method of claim 15 wherein such contacting is effected in the presence of tetrahydrofuran, whereby the solubility of the said organic compound is maximized.

* * * * *

UNITED STATES PATENT AND TRADEMARK OFFICE
CERTIFICATE OF CORRECTION

PATENT NO. : 4,533,760
DATED : August 6, 1985
INVENTOR(S) : Robert A. Benkeser et al It is certified that error appears in the above-identified patent and that said Letters Patent is hereby corrected as shown below:

Column 1, line 28, change "aromaic" to --aromatic--.

Column 2, line 2, change "preverably" to --preferably--.

Column 4, line 46, change "(6)" to --(6%)--

Column 5, line 5, insert --and-- between "1" and "2".

Signed and Sealed this

Twenty-second Day of July 1986

[SEAL]

Attest:

DONALD J. QUIGG

Attesting Officer          Commissioner of Patents and Trademarks